United States Patent [19]

Holland

[11] 4,009,384
[45] Feb. 22, 1977

[54] LAMP SCENT UNIT
[75] Inventor: Ada R. Holland, Atlanta, Ga.
[73] Assignee: The Raymond Lee Organization, Inc., New York, N.Y.; a part interest
[22] Filed: Mar. 10, 1975
[21] Appl. No.: 556,888
[52] U.S. Cl. .................. 240/108 R; 21/120; 239/56; 239/57; 240/2 R; 44/905
[51] Int. Cl.² ............................ A61L 9/02
[58] Field of Search ....... 240/108 R, 108 A, 108 B, 240/2 R; 239/53, 55, 56, 57; 428/445, 443, 131, 137; 21/120

[56] References Cited
UNITED STATES PATENTS

| 200,192 | 2/1878 | Halpine | 428/445 |
|---|---|---|---|
| 1,655,248 | 1/1928 | Sharp | 239/56 |
| 1,920,599 | 8/1933 | Schuh | 21/120 |
| 2,121,575 | 6/1938 | Shoemaker | 240/108 |
| 2,143,246 | 1/1939 | McGary | 21/120 |
| 2,372,371 | 3/1945 | Eisner | 21/120 |
| 2,468,164 | 4/1949 | Brewster | 21/120 |
| 2,535,802 | 12/1950 | Lisbon | 21/120 |
| 2,741,812 | 4/1956 | Tellier | 21/120 |
| 2,741,813 | 4/1956 | Rubin | 21/120 |
| 2,979,268 | 4/1961 | Brun | 239/55 |
| 3,595,607 | 1/1969 | Gores | 239/57 |

Primary Examiner—George F. Lesmes
Assistant Examiner—R. J. Roche
Attorney, Agent, or Firm—Howard I. Podell

[57] ABSTRACT

A device for installing on an electric lamp to produce a pleasing scent. The device is in the form of a folded section of asbestos sheet, or other porous high temperature-resistant material, which encloses a sheet of porous fabric material which has been immersed in a solution of scented bath oil, perfume or cologne. A center hole in the device permits its installation on the frame of the shade of an electric lamp about the finial post of the lamp.

1 Claim, 5 Drawing Figures

LAMP SCENT UNIT

SUMMARY OF THE INVENTION

My invention is a device for installing on an electric lamp to produce a pleasing scent. The device is in the form of a folded section of asbestos sheet, or other porous high temperature-resistant material, which encloses a sheet of porous fabric material which has been immersed in a solution of scented bath oil, perfume or cologne. A center hole in the device permits its installation on the frame of the shade of an electric lamp about the finial post of the lamp.

BRIEF DESCRIPTION OF THE DRAWINGS

The objects and features of the invention may be understood with reference to the following detailed description of an illustrative embodiment of the invention, taken together with the accompanying drawings in which.

DESCRIPTION OF THE PREFERRED EMBODIMENT

Figure 1:
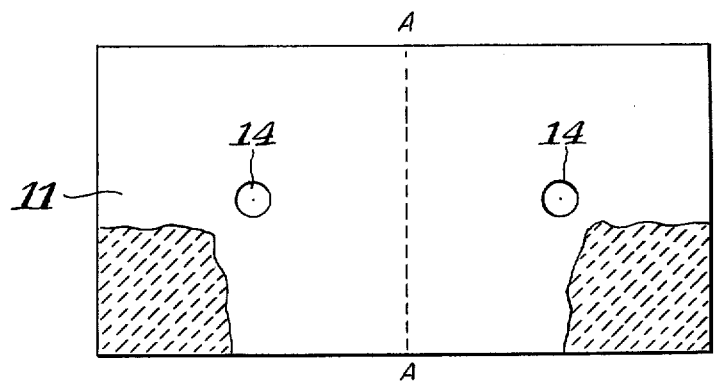
FIG. 1 is a plan view of the outer sheet, prior to folding.
Figure 2:
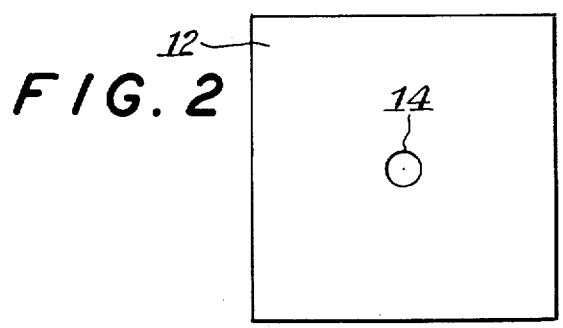
FIG. 2 is a plan view of the inner sheet, prior to assembly.
Figure 3:
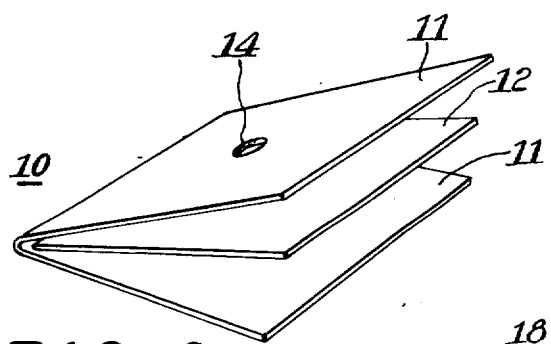
FIG. 3 is a perspective use of the assembly, prior to installation on a lamp.
Figure 4:
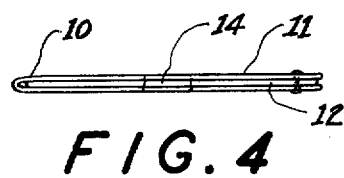
FIG. 4 is a side view of the assembly, prior to installation on a lamp.
Figure 5:
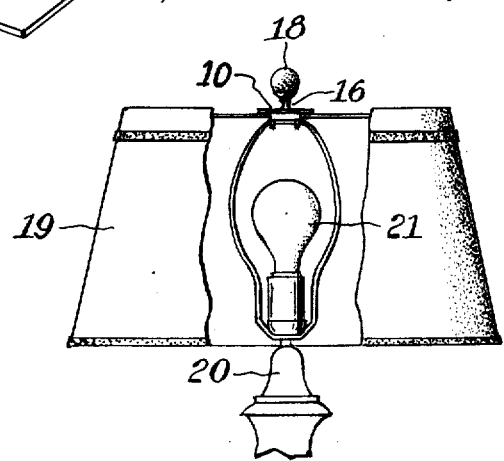
FIG. 5 is an elevation view of the invention in use.

Turning now descriptively to the drawings, in which similar reference characters denote similar elements throughout the several views, FIGS. 1-5 illustrate the device 10 which is formed of an outer sheet 11 of high temperature-resistant insulation material such as asbestos paper that is folded about line A—A to form a square object enclosing a square sheet 12 of a porous fabric which has been immersed in a solution of scent such as bath oil. Both sheets 11 and 12 are fitted with holes that form a center hole in the assembled piece 10 of a size to fit over the male terminal screw post 16 of an electric lamp 20 that serves to engage the lamp shade 19 and finial 18.

The device 10 is assembled to a lamp 20 by removing the finial 18 and placing the folded device 10 over the male screw 16 and replacing the finial 18. Heat from the lamp bulb 21 serves to vaporize the scent impregnated in inner sheet 12 in a gradual fashion. The thermal insulation effect of the outer sheet 11 prevents undue heating and excessive drying of the solution impregnated in inner sheet 12 to provide a long lasting effect.

Sheet 12 may be immersed in scented bath oil, perfumes or cologne, prior to assembly, but the most long lasting effects have been obtained with solutions such as bath oils which have a higher temperature of evaporation than conventional solutions of colognes and perfumes.

Since obvious changes may be made in the specific embodiment of the invention described herein, such modifications being within the spirit and scope of the invention claimed, it is indicated that all matter contained herein is intended as illustrative and not as limiting in scope.

Having thus described the invention, what I claim as new and desire to secure by Letters Patent of the United States is:

1. A lamp shade holder mounted to a lamp assembly, with the lamp shade holder formed to fit about and over a lamp bulb mounted in said lamp assembly, said lamp shade holder fitted with a post screw projecting from the said holder which screw projects from the holder away from a mounted lamp bulb, said screw adaptable for fitting into a finial hole of a lamp shade for attachment of the lamp shade to the said holder, together with a container unit formed with a centrally located mounting hole of a size to fit about said post screw, said container unit formed of a first sheet of porous material of high temperature-resistant and thermal insulation properties, which said first sheet is folded about an inner second sheet of porous material that is impregnated with a solution of scented material, said central mounting hole passing through the said folded first sheet and the said folded second sheet.

* * * * *